(12) United States Patent
Cheng et al.

(10) Patent No.: US 9,844,322 B2
(45) Date of Patent: Dec. 19, 2017

(54) CAMERA DEVICE AND PHOTOGRAPHING METHOD

(71) Applicant: ALTEK BIOTECHNOLOGY CORPORATION, Taipei (TW)

(72) Inventors: Shin-Hao Cheng, Taichung (TW); Pin-Wen Chen, Changhua County (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 713 days.

(21) Appl. No.: 13/778,130

(22) Filed: Feb. 27, 2013

(65) Prior Publication Data
US 2014/0192321 A1  Jul. 10, 2014

(30) Foreign Application Priority Data

Jan. 8, 2013  (TW) .............................. 102100591 A

(51) Int. Cl.
*A61B 3/14* (2006.01)
*A61B 3/12* (2006.01)

(52) U.S. Cl.
CPC . *A61B 3/14* (2013.01); *A61B 3/12* (2013.01)

(58) Field of Classification Search
CPC ........................................................ A61B 3/14
USPC ................................................ 351/206, 246
See application file for complete search history.

(56) References Cited

U.S. PATENT DOCUMENTS

| 2008/0231803 | A1 | 9/2008 | Feldon et al. |
| 2012/0002165 | A1 | 1/2012 | Saito |
| 2013/0093998 | A1* | 4/2013 | Bishop .................. A61B 3/107 351/208 |

FOREIGN PATENT DOCUMENTS

TW         201224635         6/2012

OTHER PUBLICATIONS

"Office Action of Taiwan Counterpart Application", dated Oct. 13, 2015, p. 1-p. 4.

* cited by examiner

*Primary Examiner* — Jack Dinh
(74) *Attorney, Agent, or Firm* — JCIPRNET

(57) ABSTRACT

A camera device configured to obtain an image of an eye is provided. The camera apparatus includes an image sensing unit, a lens set, and a processing unit. The lens set is located between the image sensing unit and the eye and projects light from the eye to the image sensing unit. Here, the lens set and the image sensing unit correspondingly move relative to the eye and continuously shoot a plurality of images of a plurality of parts of the eye. The processing unit is electrically connected to the image sensing unit, and the processing unit stitches the images. A photographing method is also provided.

9 Claims, 6 Drawing Sheets

CAMERA DEVICE AND PHOTOGRAPHING METHOD

CROSS-REFERENCE TO RELATED APPLICATION

This application claims the priority benefit of Taiwan application serial no. 102100591, filed on Jan. 8, 2013. The entirety of the above-mentioned patent application is hereby incorporated by reference herein and made a part of this specification.

BACKGROUND OF THE INVENTION

Field of the Invention

The invention relates to a camera device and a photographing method.

Description of Related Art

People nowadays often unknowingly show signs of strained vision because of reading or watching screens with their eyes, and thus more and more people suffer from ophthalmic diseases. Among the ophthalmic diseases, retinal detachment, macular hemorrhage, or blood vessel hyperplasia may cause irreversible damages to eyes of a patient. Therefore, ocular fundus examinations on retinas, macula lutea, and optic discs located at fundi of eyes always play a decisive role in eye care.

Since the retinas, the macula lutea, and the optic discs are all located at the fundi of the eyes, the ocular fundus examinations are frequently performed by observing the fundi or shooting images of the fundi through pupils of the eyes. However, the size of the pupil of a normal human eye is rather small, and thus it is difficult to obtain the complete look of the fundus in one image-shooting step. When the ocular fundus examination is performed in the real world, paramedics often ask the patient to stare at one fixed point and then slowly change the direction of the stare, such that the paramedics may be allowed to take photographs of the fundus at different angles. Nevertheless, the photographs of the fundus separately taken at different time points may have different levels of exposure, which is not conducive to the subsequent step of stitching images of the fundus. Moreover, in the process of separately taking the photographs of the fundus at different time points, the paramedics and the patient are burdened with the significant time consumed on taking the images of the fundus, and temporary ophthalmodonesis (i.e., trembling motion of the eye) may even occur, such that the shot images of the fundus are blurred. As a result, how to efficiently take wide-field photographs of the fundus as the referential information for clinical diagnosis of ophthalmic diseases is one of the issues to be resolved as soon as possible.

SUMMARY OF THE INVENTION

The invention is directed to a camera device that is able to expand the field of images of an eye in an efficient manner.

The invention is directed to a photographing method that is able to expand the field of images of an eye in an efficient manner.

In an embodiment of the invention, a camera device configured to obtain an image of an eye is provided. The camera device includes an image sensing unit, a lens set, and a processing unit. The lens set is located between the image sensing unit and the eye and projects light from the eye to the image sensing unit. Here, the lens set and the image sensing unit correspondingly move relative to the eye and continuously shoot a plurality of images of a plurality of parts of the eye. The processing unit is electrically connected to the image sensing unit, and the processing unit stitches the images.

According to an embodiment of the invention, the lens set includes a first axis movable lens set which has a first optical axis. The first optical axis of the first axis movable lens is translated relative to an optical axis of the eye. The image sensing unit is moved corresponding to the translation of the first axis movable lens set, and the image sensing unit continuously shoots the images of the parts of the eye.

According to an embodiment of the invention, the camera device further includes a first actuation module that is connected to the first axis movable lens set to move the first axis movable lens set.

According to an embodiment of the invention, the first actuation module includes a piezoelectric actuator or a motor.

According to an embodiment of the invention, the lens set further includes a second axis movable lens set that is located between the first axis movable lens set and the eye. The second axis movable lens set includes a second optical axis that is rotated relative to the optical axis of the eye, so as to change an included angle between the second optical axis and the optical axis of the eye and to point the second optical axis at the parts of the eye, and light from the parts of the eye is transmitted to the image sensing unit sequentially through the second axis movable lens set and the first axis movable lens set.

According to an embodiment of the invention, the camera device further includes a second actuation module that is connected to the second axis movable lens set, so as to translate and rotate the second axis movable lens set. Here, the translation and the rotation of the second axis movable lens set correspond to the translation of the first axis movable lens set.

According to an embodiment of the invention, the camera device further includes a third actuation module that is connected to the image sensing unit, so as to move the image sensing unit. The processing unit controls the first actuation module, the second actuation module, and the third actuation module, such that the movement of the image sensing unit corresponds to the translation of the first axis movable lens set and corresponds to the translation and the rotation of the second axis movable lens set.

According to an embodiment of the invention, the parts of the eye are parts of a fundus of the eye, and light from the fundus is transmitted to the image sensing unit sequentially through a pupil of the eye and the lens set.

According to an embodiment of the invention, the processing unit determines a moving distance of the lens set relative to the eye according to a size of a pupil of the eye.

According to an embodiment of the invention, the shot parts of the eye are partially overlapped with one another.

In an embodiment of the invention, a camera device configured to obtain an image of an eye is provided. The camera device includes an image sensing unit, a first axis movable lens set, and a second axis movable lens set. The first axis movable lens set has a first optical axis which is translated relative to an optical axis of the eye. The image sensing unit is moved corresponding to the translation of the first axis movable lens set, and the image sensing unit continuously shoots a plurality of images of a plurality of parts of the eye. The second axis movable lens set is located between the first axis movable lens set and the eye and has a second optical axis that is rotated relative to the optical axis of the eye, so as to change an included angle between the second optical axis and the optical axis of the eye and to point the second optical axis at the parts of the eye, and light from the parts of the eye is transmitted to the image sensing unit sequentially through the second axis movable lens set and the first axis movable lens set.

According to an embodiment of the invention, the camera device further includes a processing unit that is electrically connected to the image sensing unit. The processing unit determines moving distances of both the first axis movable lens set and the second axis movable lens set relative to the eye according to a size of a pupil of the eye.

In an embodiment of the invention, a photographing method is provided, and the photographing method includes: simultaneously and correspondingly moving a lens set and an image sensing unit in a continuous image-shooting process, such that the image sensing unit obtains a plurality of images of a plurality of parts of an eye; and stitching the images of the parts of the eye.

According to an embodiment of the invention, the photographing method further includes determining a plurality of axis moving positions of the lens set relative to the eye according to a size of a pupil of the eye.

According to an embodiment of the invention, the photographing method further includes determining whether moving directions of the lens set and the image sensing unit are horizontal or vertical before determining the axis moving positions of the lens set relative to the eye according to the size of the pupil of the eye.

According to an embodiment of the invention, the lens set includes a first axis movable lens set and a second axis movable lens set, and the second axis movable lens set is located between the first axis movable lens set and the eye. In the photographing method, the step of simultaneously and correspondingly moving the lens set and the image sensing unit further includes: moving the first axis movable lens set to the axis moving positions sequentially; moving and rotating the second axis movable lens set; moving the image sensing unit and causing the movement of the first axis movable lens set, the movement and the rotation of the second axis movable lens set, and the movement of the image sensing unit to correspond to one another.

According to an embodiment of the invention, when the first axis movable lens set is moved toward one of the axis moving positions, the photographing method further includes determining whether the first axis movable lens set is moved to the one of the axis moving positions with use of a photo-interrupter. If the first axis movable lens set is not moved to the one of the axis moving positions, the photographing method further includes proceeding to move the first axis movable lens set until the first axis movable lens arrives at the one of the axis moving positions.

In view of the above, the lens set and the image sensing unit in the camera device described herein are moved relative to the eye and shoot images of a plurality of parts of the eye in a continuous manner, and the images are then stitched. Thereby, the wide-field images of the eye may be rapidly taken. Besides, in the camera device described herein, the first axis movable lens set, the second axis movable lens set, and the image sensing unit that are moved correspondingly may be employed to shoot images of a plurality of parts of the eye in a continuous manner. Thereby, images of multiple parts of the eye may be rapidly obtained. Additionally, according to the photographing method described herein, images of a plurality of parts of an eye may be obtained and stitched in one continuous image-shooting process. Thereby, the image-shooting efficiency may be improved, and the field of the shot images may be expanded.

In order to make the aforementioned and other features and advantages of the invention more comprehensible, embodiments accompanying figures are described in detail below.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
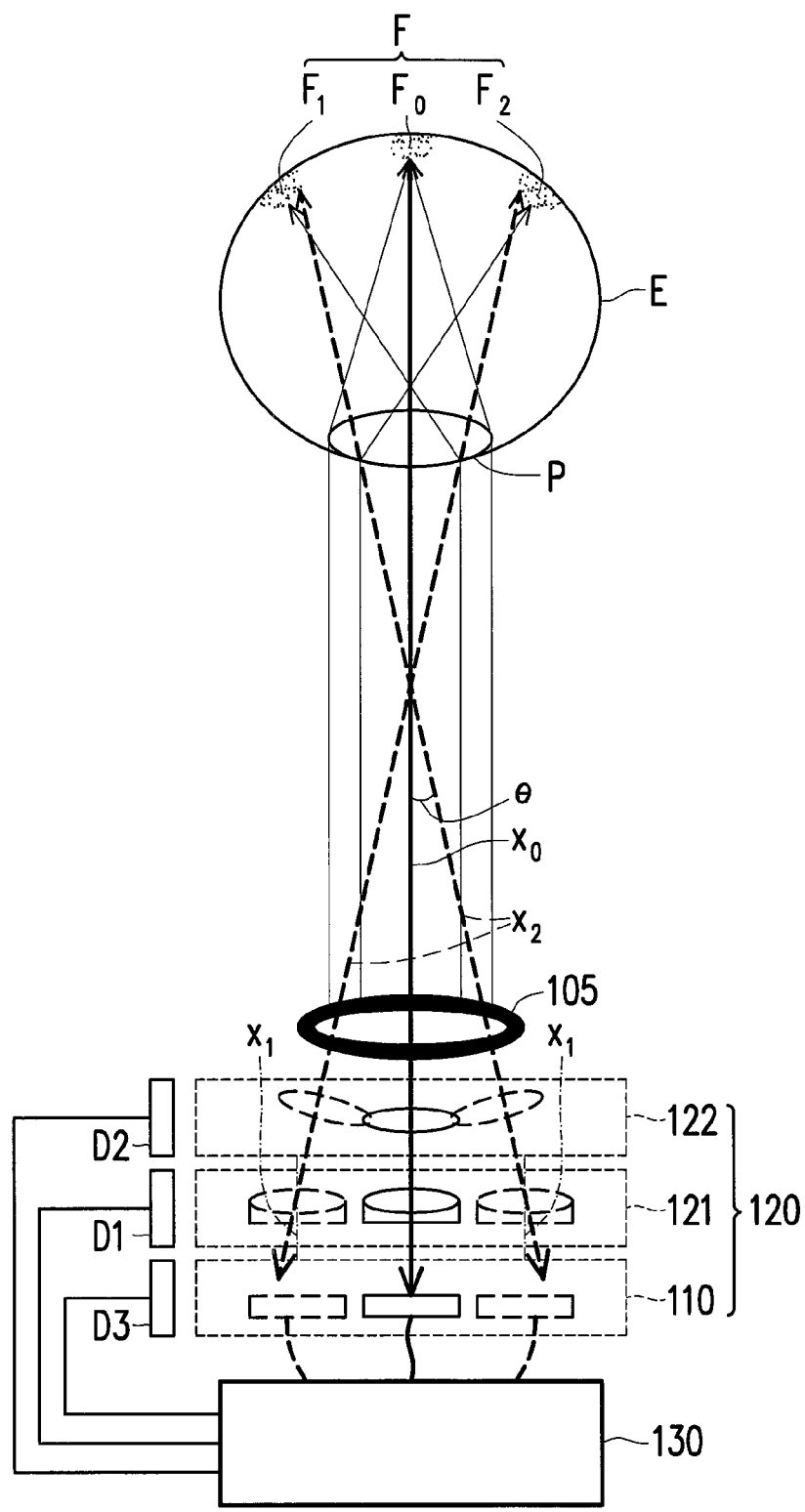
FIG. 1 is a schematic view illustrating a camera device according to an embodiment of the invention.

FIG. 1 is a schematic view illustrating a camera device according to an embodiment of the invention. With reference to FIG. 1, in the present embodiment, the camera device 100 is configured to obtain an image of an eye E, and the camera device 100 includes an image sensing unit 110 and a lens set 120. The lens set 120 is located between the image sensing unit 110 and the eye E and projects light from the eye E to the image sensing unit 110. Here, the lens set 120 and the image sensing unit 110 correspondingly move relative to the eye E and continuously shoot a plurality of images of a plurality of parts of the eye E. In the present embodiment, the way to continuously shoot the images refers to the way to continuously shoot the images at predetermined time intervals in the functions of the camera, i.e., the way to continuously shoot the images by pressing a shooting button once. When the predetermined time interval is small, the images taken may be considered as the images that are continuously shot. Here, the time interval at which the images are continuously taken falls within the range from 200 microseconds to 330 microseconds.

The camera device 100 described in the present embodiment further includes a processing unit 130 that is electrically connected to the image sensing unit 110, and the processing unit 130 may stitch the images. Here, as shown in FIG. 1, the parts of the eye E are a plurality of parts $F_0$, $F_1$, and $F_2$ of a fundus F of the eye E, for instance, and light from the fundus F is transmitted to the image sensing unit 110 sequentially through a pupil P of the eye E and the lens set 120. Thereby, the images of the parts (e.g., $F_0$, $F_1$, and $F_2$) of the fundus F of the eye E may be continuously taken by the image sensing unit 110 and the lens set 120 that are moved relative to the parts (e.g., $F_0$, $F_1$, and $F_2$) of the fundus F in one continuous image-shooing process and then be stitched to form an image of the fundus F with wider field. Since the images of the fundus F are obtained by performing the continuous image-shooing process, these images have similar image conditions (e.g., the level of exposure, color tone, etc.), which is conducive to improvement of the efficiency and accuracy of the subsequent image stitching process. Moreover, the correctness of clinical diagnosis may also be enhanced. The shot parts of the eye E may be partially overlapped with one another; thus, the accuracy of the image stitching process may be enhanced, and paramedics are able to diagnose ophthalmic diseases efficiently and correctly.

In particular, the lens set 120 includes a first axis movable lens set 121 and a second axis movable lens set 122. The first axis movable lens set 121 has a first optical axis $x_1$ which is translated relative to an optical axis $x_0$ of the eye E. The image sensing unit 110 is moved corresponding to the translation of the first axis movable lens set 121, and the image sensing unit 110 continuously shoots the images of the parts of the eye E. The second axis movable lens set 122 is located between the first axis movable lens set 121 and the eye E. The second axis movable lens set 121 has a second optical axis $x_2$ that is rotated relative to the optical axis $x_0$ of the eye E, so as to change an included angle θ between the second optical axis $x_2$ and the optical axis $x_0$ of the eye E and to point the second optical axis $x_2$ at the parts (e.g., the parts $F_0$, $F_1$, and $F_2$ of the fundus F shown in FIG. 1) of the eye E, and light from the parts of the eye E is transmitted to the image sensing unit 110 sequentially through the second axis movable lens set 122 and the first axis movable lens set 121.

For instance, according to the present embodiment, the fundus F of the eye E has diopter, i.e., the surface of the fundus F is a curved surface; therefore, when the parts of the fundus F are detected in the directions of optical axes different from the direction of the optical axis $x_0$ of the eye E, the distortion (e.g., keystone distortion) may occur, which negatively affects the possibility of recognizing blood vessels, optic discs, or other ocular organs in the images. In the present embodiment, the first optical axis $x_1$ of the first axis movable lens set 121 is translated relative to the optical axis $x_0$ of the eye E, so as to correct or reduce image deviations generated by the translation of the first optical axis $x_1$ with respect to the optical axis $x_0$ of the eye E. In another aspect, the second optical axis $x_2$ of the second axis movable lens set 122 is rotated relative to the optical axis $x_0$ of the eye E to change the included angle θ between the second optical axis $x_2$ and the optical axis $x_0$ of the eye E. Thereby, the second axis movable lens set 122 is capable of collecting the light emitted from the pupil P at different angles, and the camera device 100 is then able to obtain the images of different parts of the fundus F. The image sensing unit 110 moves (e.g. translates) corresponding to the translation of the first axis movable lens set 121 and continuously shoots the images of the parts of the eye E. As such, the calibrated images of the parts of the fundus F may be well imaged on the image sensing unit 110 for performing the subsequent image stitching process. Therefore, in the present embodiment, the distortion and aberration of images of the parts (e.g., the parts $F_0$, $F_1$, and $F_2$ shown in FIG. 1) of the fundus F may be calibrated in one image-shooting process by the first axis movable lens set 121 and the second axis movable lens set 122, and the images of the parts (e.g., the parts $F_0$, $F_1$, and $F_2$ shown in FIG. 1) of the fundus F may be continuously taken by the image sensing unit 110. As such, the time spent on taking the images may be reduced, and the image quality may be improved, which are conducive to the subsequent image stitching process and the diagnosis by the paramedics.

To be more specific, in the present embodiment, the camera device 100 may further include a first actuation module D1, a second actuation module D2, and a third actuation module D3. The first actuation module D1 is connected to the first axis movable lens set 121 to translate the first axis movable lens set 121. The second actuation module D2 is connected to the second axis movable lens set 122 to translate and rotate the second axis movable lens set 122. Here, the translation and the rotation of the second axis movable lens set 122 correspond to the translation of the first axis movable lens set 121. The third actuation module D3 is connected to the image sensing unit 110 to translate the image sensing unit 110. According to the present embodiment, the processing unit 130 is electrically connected to and controls the first actuation module D1, the second actuation module D2, and the third actuation module D3, such that the translation of the image sensing unit 110 corresponds to the translation of the first axis movable lens set 121 and corresponds to the translation and the rotation of the second axis movable lens set 122. In the present embodiment, each of the first actuation module D1, the second actuation module D2, and the third actuation module D3 may include a piezoelectric actuator or a motor. The processing unit 130 determines a moving distance of the lens set 120 relative to the eye E according to a size of the pupil P of the eye E and determines the relative movement correlations among the first axis movable lens set 121, the second axis movable lens set 122, and the image sensing unit 110 according to the moving distance. Besides, through the first actuation module D1, the second actuation module D2, and the third actuation module D3 controlled by the processing unit 130, the images of the parts of the eye E may be shot and calibrated. In another embodiment, the first axis movable lens set 121, the second axis movable lens set 122, and the image sensing unit 110 may be connected by a linkage mechanism, and an actuator may be employed to drive one of the first axis movable lens set 121, the second axis movable lens set 122, the image sensing unit 110, and the linkage mechanism. By means of the linkage of the linkage mechanism, when one of the first axis movable lens set 121, the second axis movable lens set 122, the image sensing unit 110, and the linkage mechanism is driven to move, the other three are correspondingly moved as well.

In the present embodiment, the first axis movable lens set 121 includes one lens, and the second axis movable lens set 122 also includes one lens, for instance. However, in other embodiments, the first axis movable lens set 121 may include a plurality of lenses, and so may the second axis movable lens set 122.

According to the present embodiment, the camera device 100 further includes an illumination light source 105 disposed next to the lens set 120. In FIG. 1, the illumination light source 105 is located in front of the lens set 120, for instance. The illumination light source 105 is configured to provide illumination light to the eye E, and thereby the illumination required by the image-shooting process is ensured. For instance, the illumination light source 105 may be a ring-shaped flash lamp. However, in other embodiments, the illumination light source 105 may also be in another shape or may be an invisible light source.

Figure 2A:
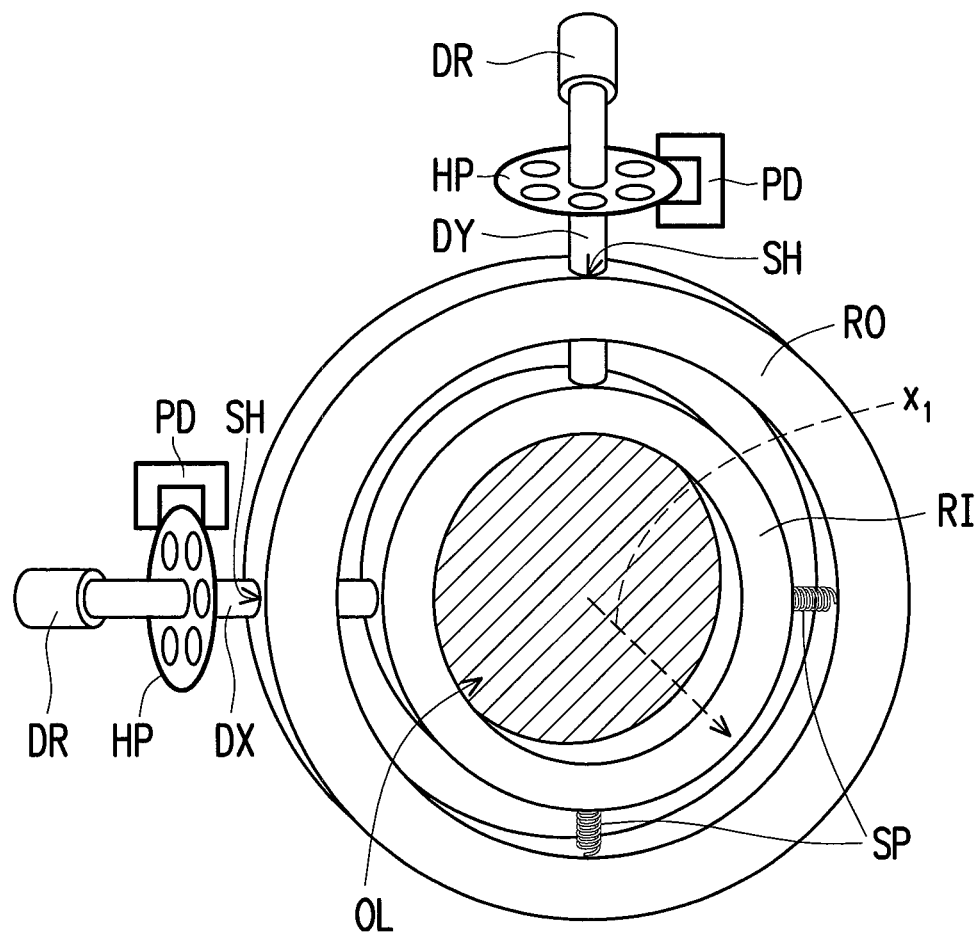
FIG. 2A is a schematic view illustrating a second actuation module according to the embodiment depicted in FIG. 1.

FIG. 2A is a schematic view illustrating a second actuation module according to the embodiment depicted in FIG. 1. With reference to FIG. 1 and FIG. 2A, the second actuation module D2 may be as exemplarily shown in FIG. 2A, and the processing unit 130 may control a motor DR to drive a first driving device DX and a second driving device DY to be screwed into or out of threaded holes SH on an external device RO. Particularly, one end of the first driving device DX leans against an internal device RI, and force balance may be achieved by pushing the internal device RI and a spring SP, so as to adjust the relative position of the internal device RI in the external device RO. On the other hand, the second driving device DY is connected to the internal device RI, and an angle at which the internal device RI is tilted in the external device RO may be adjusted by screwing the second driving device DY into or out of the external device RO. That is, the first driving device DX allows the internal device RI to move, and the second driving device DY allows the internal device RI to rotate and tilt. Specifically, each of the first driving device DX and the second driving device DY may have a porous rotatable disk HP that may be rotated together with the rotation of the first and second driving devices DX and DY. When the first driving device DX and the second driving device DY are screwed into or out of the external device RO, the porous rotatable disk HP may be rotated, such that pores on the porous rotatable disk HP sequentially pass through a photo-interrupter PD. According to the number of the pores passing through the photo-interrupter PD, the photo-interrupter PD may determine the degree to which the first and second driving devices DX and DY are screwed into or out of the external device RO. Thereby, the location and the rotation angle of the internal device RI may be inspected, and such information may be transmitted to the processing unit 130 for feedback control. In addition, an optical lens set OL of the first axis movable lens set 121 may be located in the internal device RI. The processing unit 130 may thereby control the location of the optical lens set OL in the first axis movable lens set 121 to change the location of the first optical axis $x_1$ with respect to the optical axis $x_0$ of the eye E, such that images of the parts of the fundus F of the eye E may be further taken by the image sensing unit 110.

Figure 2B:
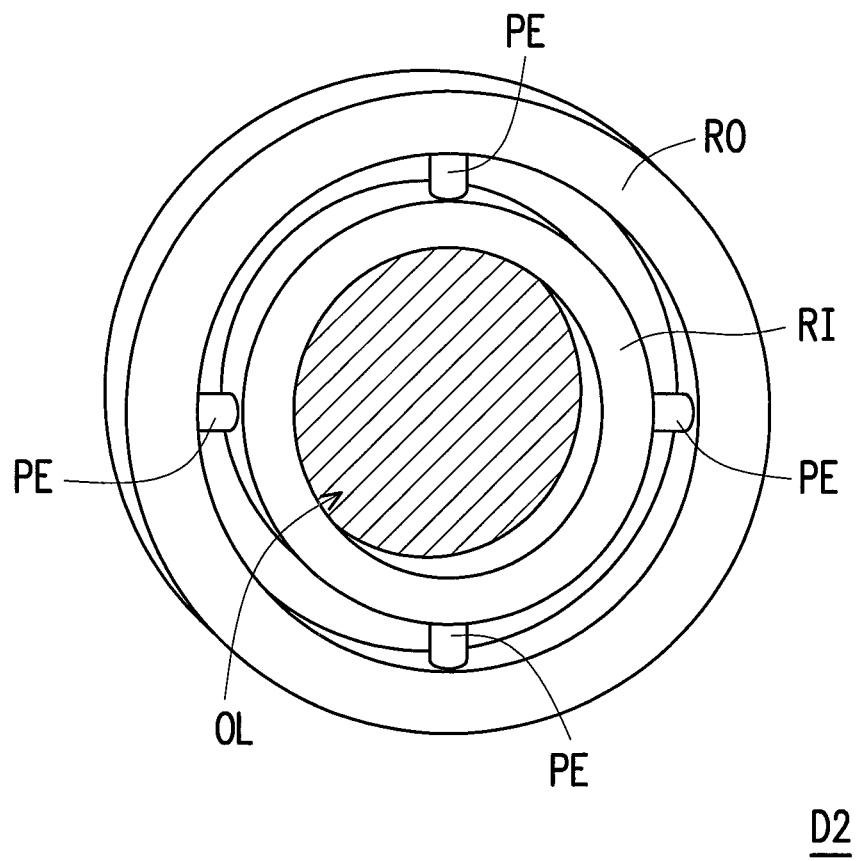
FIG. 2B is a schematic view illustrating a variation in the second actuation module according to the embodiment depicted in FIG. 1.

FIG. 2B is a schematic view illustrating a variation in the second actuation module according to the embodiment depicted in FIG. 1. With reference to FIG. 2B, for instance, the second actuation module D2 may be as exemplarily shown in FIG. 2B, a piezoelectric device PE between the external device RO and the internal device RI is electrically connected to the processing unit 130, and the piezoelectric device PE may be driven by a voltage, such that the volume of the piezoelectric device PE is changed, and that the location and the angle of the internal device RI in the external device RO may be changed. Thereby, the second actuation module D2 shown in FIG. 2B may achieve the effects similar to those that may be accomplished by the second actuation module D2 shown in FIG. 2A. What is more, the structures and the functions of the first actuation module D1 and the third actuation module D3 may be similar to those of the second actuation module D2. However, the structures of the second actuation module D2 as shown in FIGS. 2A and 2B are merely exemplary, and the structures of the first, second, and third actuation modules D1, D2, and D3 in other embodiments of the invention may be varied according to actual design, which should not be construed as a limitation to the invention.

Figure 3:
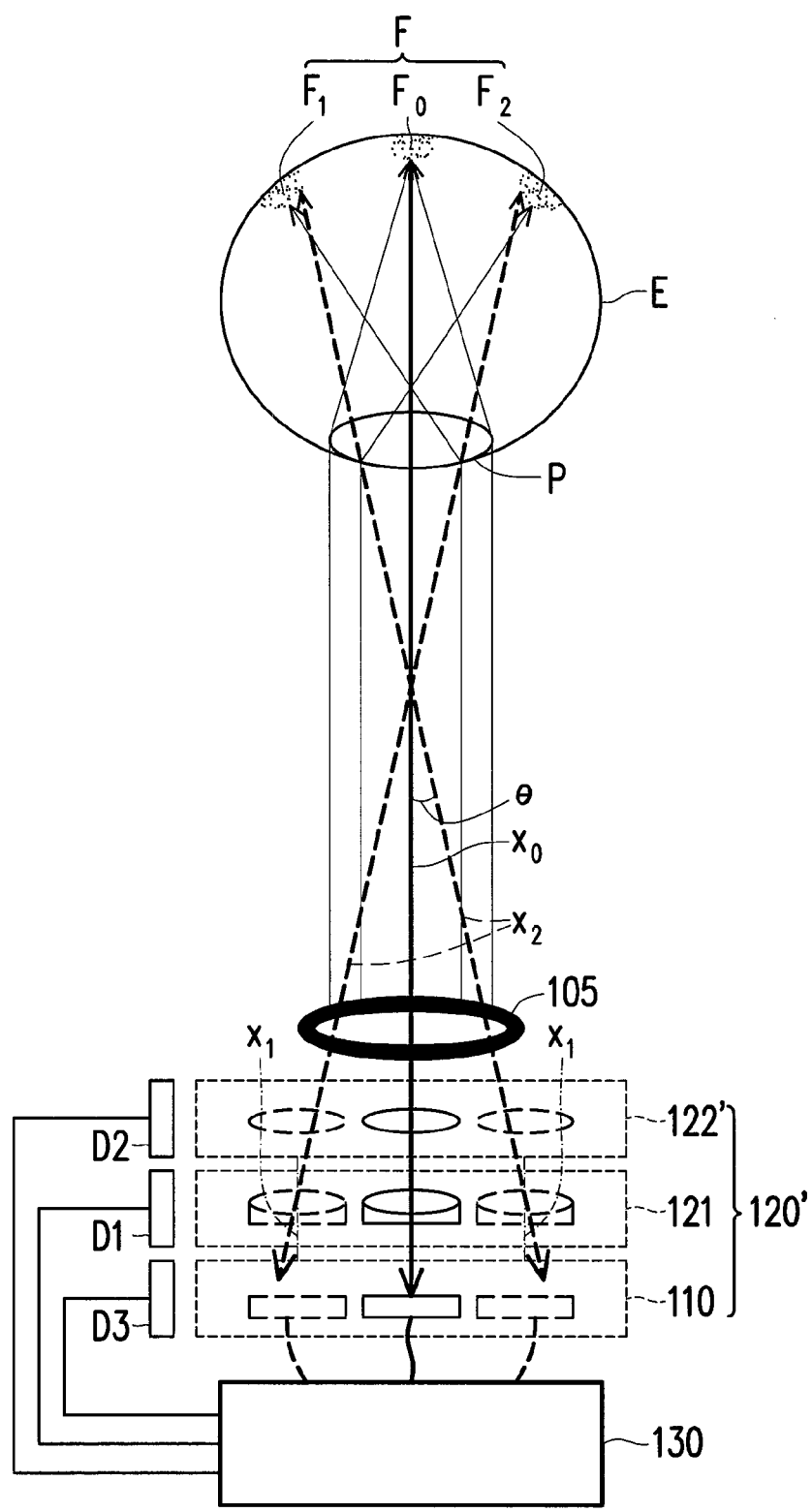
FIG. 3 is a schematic view illustrating a camera device according to another embodiment of the invention.

FIG. 3 is a schematic view illustrating a camera device according to another embodiment of the invention. With reference to FIG. 3, the camera device 100' depicted herein is similar to the camera device 100 depicted in FIG. 1, while the difference therebetween lies in that the second optical axis $x_2$ of the second axis movable lens set 122' in the camera device 100' is translated relative to the optical axis $x_0$ of the eye E but is not rotated. In addition, the first optical axis $x_1$ of the first axis movable lens set 121 and the image sensing unit 110' are translated relative to the optical axis $x_0$ of the eye E but are not rotated. Here, the translations of the second axis movable lens set 122', the first axis movable lens set 121, and the image sensing unit 110' correspond to one another. When the distance from the eye E to the first axis movable lens set 121 is rather large, the camera device 100' described in the present embodiment is applicable because the opening angle of the light from the parts of the eye E is rather small and the translated second axis movable lens set 122' is able to collect the light from the parts of the eye E.

Figure 4A:
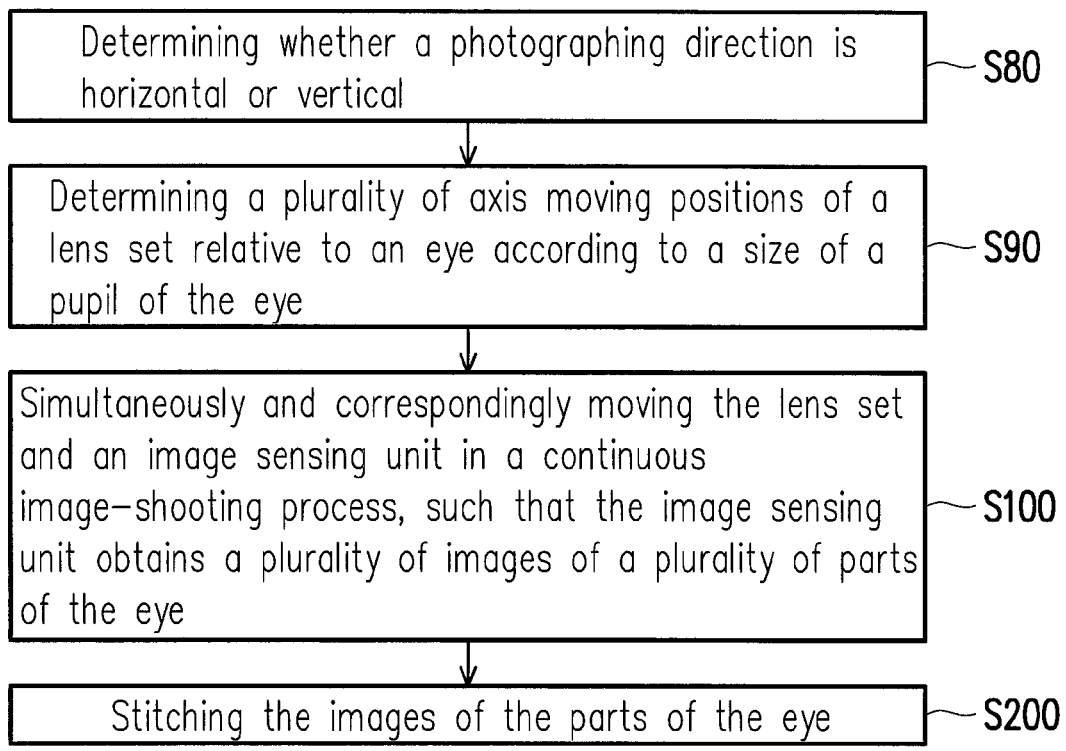
FIG. 4A is a flow chart illustrating a photographing method according to an embodiment of the invention.

FIG. 4A is a flow chart illustrating a photographing method according to an embodiment of the invention. With reference to FIG. 4A, the photographing method described in the present embodiment may be conducted with use of the camera device 100 shown in FIG. 1 or any other aforesaid camera device. The photographing method described below is exemplarily applied with use of the camera device 100. Specifically, the photographing method includes following steps. A lens set 120 and an image sensing unit 110 are simultaneously and correspondingly moved in a continuous image-shooting process, such that the image sensing unit 110 obtains a plurality of images of a plurality of parts (e.g., the parts $F_0$, $F_1$, and $F_2$ of the fundus F shown in FIG. 1) of an eye E (step S100). The images of the parts of the eye E are then stitched (step S200). According to the photographing method described herein, the images of the parts of the fundus F of the eye E may be obtained in one continuous image-shooting process, such that the time spent on taking the images may be reduced, the image-shooting efficiency may be enhanced, the burden of a patient may be alleviated, and the diagnosis by the paramedics may be efficacious. Descriptions regarding the detailed devices used in the photographing method and the effects may be referred to as those of the camera device 100 shown in FIG. 1 and will not be provided hereinafter.

According to the present embodiment, the photographing method further includes determining whether the photographing direction is horizontal or vertical before determining axis moving positions of the lens set 120 relative to the eye E according to the size of the pupil P of the eye E (step S80). That is, the images of the parts (e.g., the parts $F_0$, $F_1$, and $F_2$ of the fundus F shown in FIG. 1) of the eye E may be obtained by performing the photographing method described in the present embodiment in a vertical direction or a horizontal direction; thereby, the processing unit 130 may stitch the images rapidly in the vertical direction or the horizontal direction. Moreover, the parts of the eye E may be partially overlapped with one another, thus improving the efficiency and accuracy of stitching the wide-field images of the fundus F.

According to the present embodiment, the photographing method further includes determining the axis moving positions of the lens set 120 relative to the eye E according to the size of the pupil P of the eye E (step S90). Since the size of the pupil P of the eye P may alter, the fields of the shot images of the fundus F may also be changed. In the present embodiment, step S90 may be performed to determine the size of the pupil P and correspondingly determine the location to which the lens set 120 is required to move, such that the field of the shot images of the fundus F is suitable for clinical diagnosis.

Figure 4B:
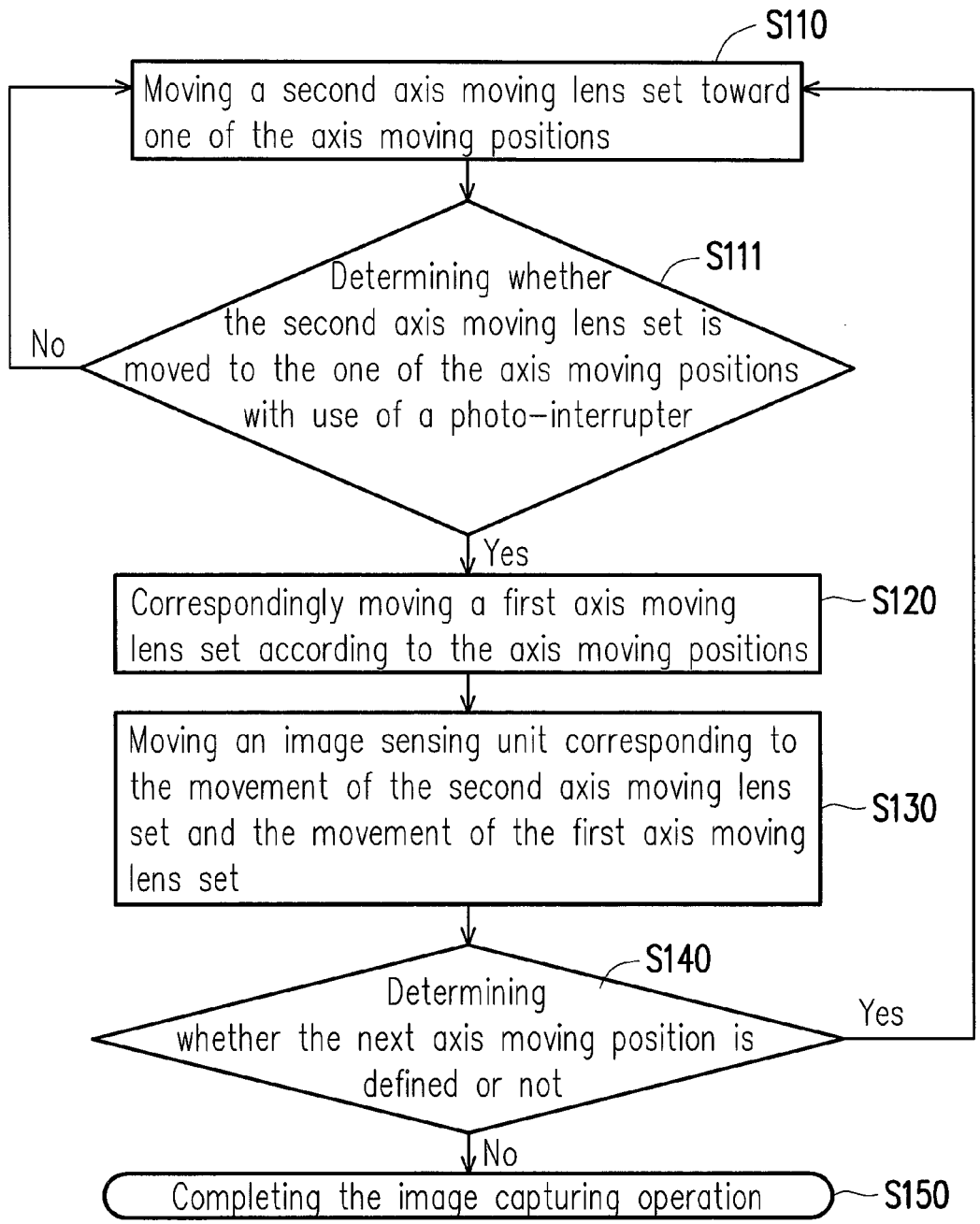
FIG. 4B is a flow chart elaborating the step S100 according to the embodiment depicted in FIG. 4A.

FIG. 4B is a flow chart elaborating the step S100 according to the embodiment depicted in FIG. 4A. In the present embodiment, the step S100 may include the following. The second axis movable lens set 122 is moved and rotated toward one of the axis moving positions (step S110). The first axis movable lens set 121 is correspondingly moved according to the axis moving positions (step S120). The image sensing unit 130 is correspondingly moved corresponding to the movement and the rotation of the second axis movable lens set 122 and the movement of the first axis movable lens set 121 (step S130). Since the required moving distances and the tilt angles of the first axis movable lens set 121, the second axis movable lens set 122, and the image sensing unit 130 may be changed under different circumstances, the steps S110, S120, and S130 may be performed to correspondingly move the first axis movable lens set 121, the second axis movable lens set 122, and the image sensing unit 130, so as to calibrate and adjust the axis movable lens sets and the distortion and aberration of images of the eye E caused by the diopter of the eye E. The correlations among the devices applied in said steps and the effects achieved thereby are described in the embodiment shown in FIG. 1 and therefore will not be explained hereinafter. Note that the order of the steps S110, S120, and S130 herein is merely exemplary, and similar effects may still be achieved in other embodiments of the invention if the steps S110, S120, and S130 are performed in other orders. The invention is not limited thereto. Moreover, in another embodiment of the invention, the steps S110, S120, and S130 may also be performed simultaneously. For instance, the processing unit 130 may simultaneously drive the first axis movable lens set 121, the second axis movable lens set 122, and the image sensing unit 130 to correspondingly move. The term "correspondingly move" described in the previous embodiments refers to that when the second axis movable lens set 122 is moved to a location where the light from a certain part of the eye E is received, the first axis movable lens set 121 is moved to a location wherein the first axis movable lens set 121 can receive the light from the certain part of the eye E, and the image sensing unit 130 is also moved to a location where the light from the certain part of the eye E can be received by the image sensing unit 130.

Besides, with reference to FIG. 1, FIG. 2A, and FIG. 4B, in the present embodiment, when the first axis movable lens set 121 is moved and rotated toward one of the axis moving positions, the step S100 may further include determining whether the first axis movable lens set 121 is moved to the one of the axis moving positions with use of a photo-interrupter PD (step S111). If the first axis movable lens set 121 is not moved to the one of the axis moving positions, the photographing method further includes proceeding to move the first axis movable lens set 121 until the first axis movable lens set 121 arrives at the one of the axis moving positions. Thereby, the movement of the first axis movable lens set 121 may be automated and monitored, so as to accurately align the parts of the fundus F of the eye E. In other embodiments of the invention, the photo-interrupter PD may be equipped with at least one of the first axis movable lens set 121, the second axis movable lens set 122, and the image sensing unit 110, so as to detect whether the at least one of the first axis movable lens set 121, the second axis movable lens set 122, and the image sensing unit 110 is moved to the correct location. However, the invention is not limited thereto. In step S111, the piezoelectric device PE controlled by the processing unit 130 (as shown in FIG. 2B) may be applied to achieve similar effects. Additionally, after step S130, whether the next axis moving position is defined or not may be determined (step S140); if yes, return to perform step S110 to move the second axis movable lens set 122 to the next axis moving position; if not, complete the image capturing operation (step S150.) The correlations among the devices applied in said steps and the effects achieved thereby are described in the embodiments shown in FIG. 2A and FIG. 2B and therefore will not be explained hereinafter.

To sum up, the lens set and the image sensing unit in the camera device described herein are moved relative to the eye and shoot images of the parts of the eye in a continuous manner, and the images are stitched. Thereby, the wide-field images of the eye may be rapidly taken, and the distortion of the images and the aberration of the images caused by the movement of the lens set may be calibrated. Moreover, according to the photographing method described herein, the images of the parts of the eye may be obtained and stitched in one continuous image-shooting process and may be calibrated. The photographing process may also be controlled by the processing unit through the photo-interrupter or a piezoelectric material. Thereby, the image-shooting efficiency may be improved, and the field of the shot images may be expanded.

It will be apparent to those skilled in the art that various modifications and variations can be made to the structure of the disclosed embodiments without departing from the scope or spirit of the invention. In view of the foregoing, it is intended that the invention cover modifications and variations of this invention provided they fall within the scope of the following claims and their equivalents.

What is claimed is:

1. A camera device configured to obtain an image of an eye, the camera device comprising:
   an image sensing unit;
   a lens set located between the image sensing unit and the eye, the lens set projecting light from the eye to the image sensing unit, wherein the lens set and the image sensing unit correspondingly move relative to the eye and continuously shoot a plurality of images of a plurality of parts of the eye, wherein the lens set comprises:
   an axis movable lens set having a first optical axis, wherein the first optical axis of the axis movable lens set is translated relative to an optical axis of the eye, the image sensing unit is moved corresponding to the translation of the axis movable lens set, and the image sensing unit continuously shoots the images of the parts of the eye; and
   a processing unit electrically connected to the image sensing unit, the processing unit stitching the images.

2. The camera device as recited in claim 1, further comprising a first actuation module connected to the axis movable lens set to move the axis movable lens set.

3. The camera device as recited in claim 2, wherein the first actuation module comprises a piezoelectric actuator or a motor.

4. The camera device as recited in claim 2, wherein the lens set further comprises:
   another axis movable lens set located between the axis movable lens set and the eye, the another axis movable lens set comprising a second optical axis rotated relative to the optical axis of the eye to change an included angle between the second optical axis and the optical axis of the eye and to point the second optical axis at the parts of the eye, wherein light from the parts of the eye is transmitted to the image sensing unit sequentially through the another axis movable lens set and the axis movable lens set.

5. The camera device as recited in claim 4, further comprising a second actuation module connected to the another axis movable lens set to translate and rotate the another axis movable lens set, wherein the translation and the rotation of the another axis movable lens set correspond to the translation of the axis movable lens set.

6. The camera device as recited in claim 5, further comprising a third actuation module connected to the image sensing unit to move the image sensing unit, wherein the processing unit controls the first actuation module, the second actuation module, and the third actuation module, such that the movement of the image sensing unit corresponds to the translation of the axis movable lens set and corresponds to the translation and the rotation of the another axis movable lens set.

7. The camera device as recited in claim 1, wherein the parts of the eye are parts of a fundus of the eye, and light from the fundus is transmitted to the image sensing unit sequentially through a pupil of the eye and the lens set.

8. The camera device as recited in claim 1, wherein the processing unit determines a moving distance of the lens set relative to the eye according to a size of a pupil of the eye.

9. The camera device as recited in claim 1, wherein the shot parts of the eye are partially overlapped with one another.

* * * * *